(12) United States Patent
Chen et al.

(10) Patent No.: US 12,038,442 B2
(45) Date of Patent: Jul. 16, 2024

(54) SAMPLE TESTING METHOD AND SAMPLE ANALYZER

(71) Applicant: Shenzhen Mindray Bio-Medical Electronics Co., Ltd., Shenzhen (CN)

(72) Inventors: Gengwen Chen, Shenzhen (CN); Ziqian Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 437 days.

(21) Appl. No.: 17/479,913

(22) Filed: Sep. 20, 2021

(65) Prior Publication Data

US 2022/0091127 A1 Mar. 24, 2022

(30) Foreign Application Priority Data

Sep. 23, 2020 (CN) .......................... 202011008754.3

(51) Int. Cl.
| | |
|---|---|
| *G01N 33/58* | (2006.01) |
| *G01N 1/30* | (2006.01) |
| *G01N 15/06* | (2006.01) |
| G01N 15/01 | (2024.01) |
| G01N 15/075 | (2024.01) |

(52) U.S. Cl.
CPC ............. *G01N 33/582* (2013.01); *G01N 1/30* (2013.01); *G01N 15/06* (2013.01); *G01N 2001/302* (2013.01); *G01N 2015/014* (2024.01); *G01N 2015/016* (2024.01); *G01N 2015/0681* (2013.01); *G01N 15/075* (2024.01)

(58) Field of Classification Search
CPC ............. G01N 33/582; G01N 33/5094; G01N 33/5091; G01N 33/80; G01N 33/56972; G01N 1/30; G01N 1/38; G01N 15/06; G01N 15/1436; G01N 15/1429; G01N 2015/0693; G01N 2015/0681; G01N 2015/1486; G01N 2015/008; G01N 2015/1006; G01N 2015/1477; G01N 2015/147; G01N 2001/302; G01N 21/47; G01N 21/6428; B01L 3/502715; B01L 2300/0654; B01L 2200/16
See application file for complete search history.

(56) References Cited

U.S. PATENT DOCUMENTS

| | | | |
|---|---|---|---|
| 9,329,172 B2 * | 5/2016 | Kimura | G01N 33/5094 |
| 11,609,175 B2 * | 3/2023 | Wang | G01N 33/5094 |
| 2017/0074863 A1 * | 3/2017 | Masuda | G01N 1/38 |

(Continued)

*Primary Examiner* — Hoa Q Pham
(74) *Attorney, Agent, or Firm* — Kory D. Christensen

(57) ABSTRACT

The disclosure provides a sample testing method and a sample analyzer, the method including: providing a sample and a reagent, the reagent including at least two fluorescent dyes for staining particles in the sample, wherein an absolute value of a difference between wavelengths corresponding to peaks of emission spectra of the two fluorescent dyes is greater than 30 nanometers and less than 80 nanometers, and an overlap between the emission spectra of the two fluorescent dyes is not greater than 50%; mixing the sample and the reagent to form a sample solution; flowing the sample solution in a flow cell in a single test, irradiating the particles flowing in the flow cell using light with a single wavelength; detecting at least fluorescence signals generated by the particles; and obtaining a test result of the sample based on at least the fluorescence signals.

18 Claims, 9 Drawing Sheets

(56) References Cited

U.S. PATENT DOCUMENTS

| | | | |
|---|---|---|---|
| 2021/0041341 A1* | 2/2021 | Chen | G01N 35/00 |
| 2021/0102935 A1* | 4/2021 | Chen | G01N 15/1429 |
| 2022/0049292 A1* | 2/2022 | Romanov | C12Q 1/6818 |
| 2023/0296591 A1* | 9/2023 | Zhang | G01N 33/80 |
| | | | 435/29 |

* cited by examiner

SAMPLE TESTING METHOD AND SAMPLE ANALYZER

CROSS-REFERENCE TO RELATED APPLICATIONS

This application claims the benefit of priority to Chinese Patent Application No. 202011008754.3, entitled "SAMPLE TESTING METHOD AND SAMPLE ANALYZER" and filed on Sep. 23, 2020, the contents of which are incorporated herein by reference.

TECHNICAL FIELD

This disclosure relates to the technical field of sample testing, and in particular, to a sample testing method and a sample analyzer.

BACKGROUND

At present, there are many methods for analyzing blood cell samples, including using a respective combination of at least two of radio frequency, high-angle scattering, low-angle scattering, impedance, side-scattered fluorescence, etc. to analyze red blood cells and white blood cells. The technology for differentiating cells by collecting fluorescence signals is currently a leading analysis technology in the world.

In currently known blood cell sample analysis methods using fluorescence, in order to obtain parameters of red blood cells, white blood cells, reticulocytes, nucleated red blood cells, etc., it is necessary to provide multiple reaction channels in a blood cell analyzer, and each channel can only be used to analyze one of the parameters. In different reaction channels, different fluorescent dyes are used to fluorescently stain blood cells, and a single exciter is then used to excite the blood cells to collect a single type of side-scattered fluorescence signals. In this process, each dye can only be used to perform specific staining for a single parameter, so as to obtain cell information.

Existing blood cell analyzers based on the fluorescence detection principle have some disadvantages: (1) white blood cells and red blood cells are measured in different channels; and (2) different dyes and reagents are used from one channel to another, resulting in a complicated liquid path structure of an instrument. Therefore, for a new generation of blood cell analyzers, there is an urgent need to reduce the types of dyes and reagents.

SUMMARY

This disclosure is provided to solve the above-mentioned problems. According to an aspect of the disclosure, a sample testing method is provided, the method including: obtaining a sample to be tested; providing a reagent, the reagent including at least two fluorescent dyes for staining particles in the sample to be tested, wherein an absolute value of a difference between wavelengths corresponding to peaks of emission spectra of the two fluorescent dyes is greater than 30 nanometers and less than 80 nanometers, and an overlap between the emission spectra of the two fluorescent dyes is not greater than 50%; mixing the sample to be tested and the reagent for reaction to form a sample solution to be tested; flowing the sample solution to be tested in a flow cell in a single test, irradiating the particles flowing in the flow cell by using light with a single wavelength such that the particles generate optical signals, and detecting at least fluorescence signals from the optical signals; and obtaining a particle test result of the sample to be tested based on at least the fluorescence signals.

According to another aspect of the disclosure, a sample analyzer is provided, the sample analyzer including: a sampling portion configured to obtain a sample to be tested and transfer the sample to be tested to a reaction portion; a reagent supply portion configured to store a reagent and supply the reagent to the reaction portion as required, wherein the reagent includes at least two fluorescent dyes for staining particles in the sample to be tested, wherein an absolute value of a difference between wavelengths corresponding to peaks of emission spectra of the two fluorescent dyes is greater than 30 nanometers and less than 80 nanometers, and an overlap between the emission spectra of the two fluorescent dyes is not greater than 50%; the reaction portion comprising a mixing chamber and being configured to mix the sample to be tested and the reagent for reaction to form a sample solution to be tested; an optical detection system, including a first light source, a flow cell and an optical signal detector, wherein the particles in the sample solution to be tested are capable of flowing in the flow cell in a single test, the first light source is configured to irradiate the particles flowing in the flow cell by using light with a single wavelength such that the particles generate optical signals, and the optical signal detector is configured to detect at least fluorescence signals from the optical signals; a transfer apparatus configured to transfer the sample solution to be tested that has been treated with the reagent in the reaction portion, to the flow cell of the optical detection system; and a processor configured to obtain a particle test result of the sample to be tested based on at least the fluorescence signals.

According to the sample testing method and the sample analyzer of the embodiments of the disclosure, a mixed dye including two fluorescent dyes is used in a particle detection of a sample to be tested. Since a difference between wavelengths corresponding to peaks of emission spectra of the two fluorescent dyes and an overlap between the emission spectra of the two fluorescent dyes are each within a respective preset range, different cells in the sample to be tested are stained by the different dyes of the mixed dye and then emit different fluorescence signals under irradiation of a single light source, so that multiple parameters of one sample to be tested can be detected in a single test (in a single reaction channel).

BRIEF DESCRIPTION OF THE DRAWINGS

The above and other objects, features and advantages of the disclosure will become more apparent from the description of embodiments of the disclosure in detail with reference to the accompanying drawings. The accompanying drawings, which are intended to provide a further understanding of embodiments of the disclosure and constitute a part of this specification, are intended to explain the disclosure together with the embodiments of the disclosure and not to limit the disclosure. In the accompanying drawings, same reference numerals generally indicate same elements or steps.

DETAILED DESCRIPTION

In order to make the objectives, technical solutions, and advantages of the disclosure more apparent, exemplary embodiments according to the disclosure will be described in detail below with reference to the accompanying drawings. The described embodiments are merely some embodiments rather than all embodiments of the disclosure. It should be understood that the exemplary embodiments described herein do not constitute any limitation to the disclosure. All other embodiments derived by those skilled in the art without creative efforts on the basis of the embodiments of the disclosure described in the disclosure shall fall within the scope of protection of the disclosure.

Figure 1:
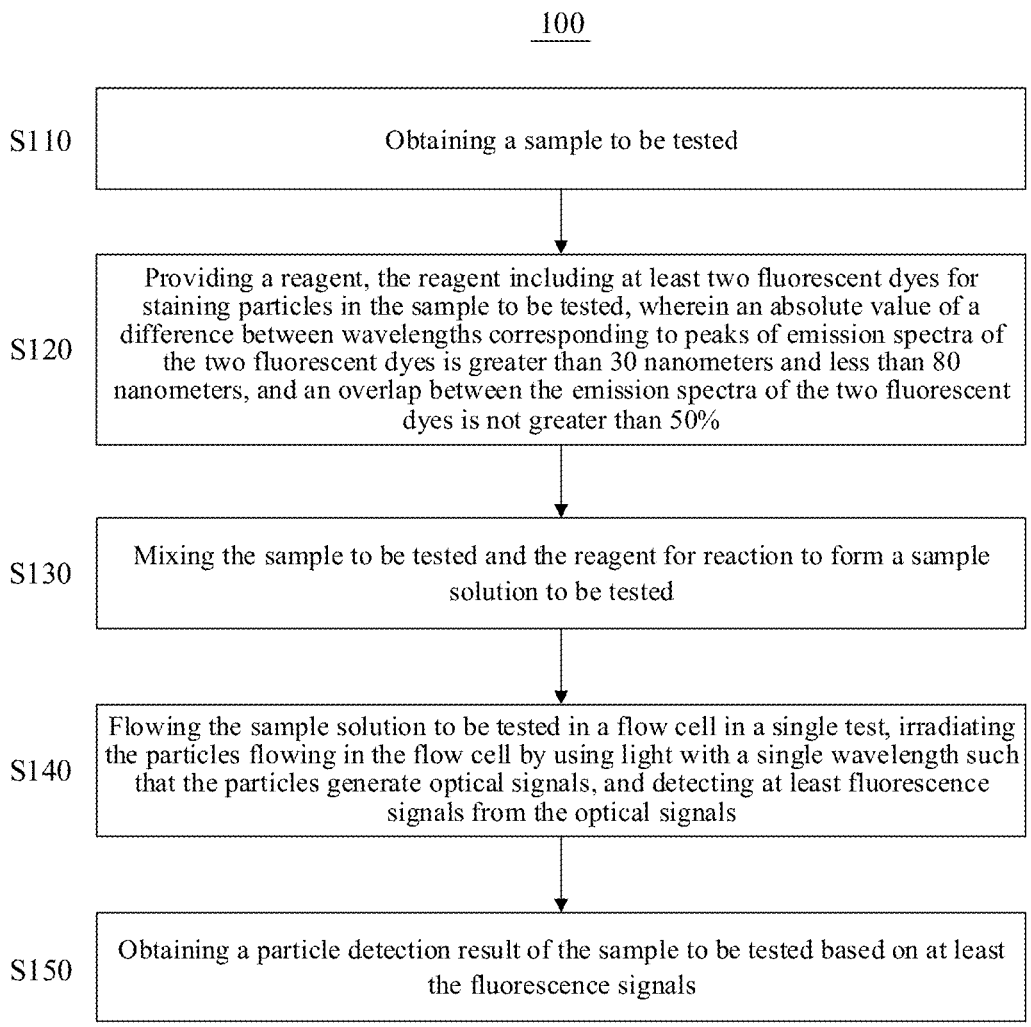
FIG. 1 shows a schematic flowchart of a sample testing method according to an embodiment of the disclosure.

First, referring to FIG. 1, a sample testing method according to an embodiment of the disclosure is described. FIG. 1 shows a schematic flowchart of a sample testing method 100 according to an embodiment of the disclosure. As shown in FIG. 1, the sample testing method 100 according to the embodiment of the disclosure may include the following steps.

In step S110, a sample to be tested is obtained.

In step S120, a reagent is provided, the reagent including at least two fluorescent dyes for staining particles in the sample to be tested. An absolute value of a difference between wavelengths corresponding to peaks of emission spectra of the two fluorescent dyes is greater than 30 nanometers and less than 80 nanometers, and an overlap between the emission spectra of the two fluorescent dyes is not greater than 50%.

In step S130, the sample to be tested and the reagent are mixed for reaction to form a sample solution to be tested.

In step S140, the sample solution to be tested are flowed in a flow cell in a single test, the particles flowing in the flow cell are irradiated by using light with a single wavelength such that the particles generate optical signals, and at least fluorescence signals are detected from the optical signals.

In step S150, a particle test result of the sample to be tested is obtained based on at least the fluorescence signals.

In one embodiment of the disclosure, a mixed dye including two fluorescent dyes is used to stain the sample to be tested (such as a blood sample) in a single reaction channel (in a single test), and a single light source (light with a single wavelength) is used to irradiate stained particles flowing in the flow cell. Since emission spectra of the two fluorescent dyes of the mixed dye meet a certain condition, different particles (such as different cells) stained by the two fluorescent dyes in the same reaction channel can emit different fluorescence signals, so that different particles can be distinguished and detected in one test. In one embodiment of the disclosure, in order to achieve the above-mentioned objectives, the applicant has determined that the emission spectra of the two fluorescent dyes included in the mixed dye should meet the following conditions: an absolute value of a difference between wavelengths corresponding to peaks of the emission spectra of the two fluorescent dyes is greater than 30 nanometers (nm) and less than 80 nanometers, and the overlap between the emission spectra of the two fluorescent dyes is not greater than 50%.

In an embodiment of the disclosure, the fluorescence signals comprise first fluorescence signals and second fluorescence signals, and obtaining a particle test result of the sample to be tested based on at least the fluorescence signals comprises: obtaining a first particle test result of the sample to be tested based on at least the first fluorescence signals; and obtaining a second particle test result of the sample to be tested, based on at least the second fluorescence signals.

In an embodiment of the disclosure, further comprising: detecting scattered light signals from the optical signals, wherein obtaining a first particle test result of the sample to be tested based on at least the first fluorescence signals further comprises: obtaining the first particle test result of the sample to be tested based on the first fluorescence signals and the scattered light signals.

In an embodiment of the disclosure, obtaining a second particle test result of the sample to be tested based on at least the second fluorescence signal further comprises: obtaining the second particle test result of the sample to be tested based on the second fluorescence signals and the scattered light signals.

Emission spectra of two fluorescent dyes included in the mixed dye according to an embodiment of the disclosure are described below in conjunction with FIG. 2.

Figure 2:
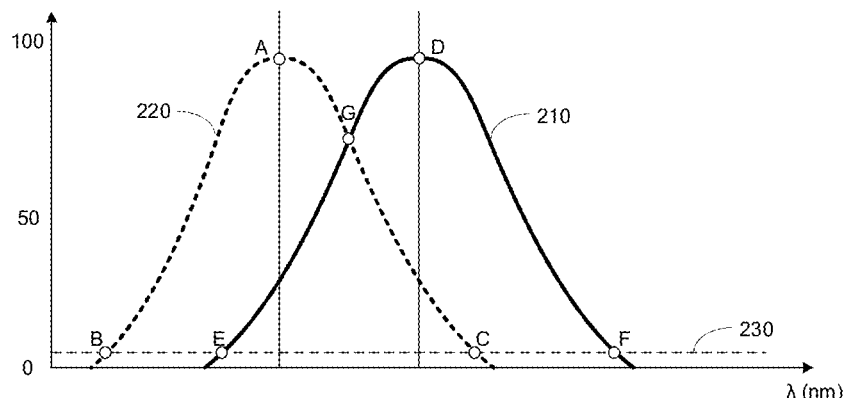
FIG. 2 shows an exemplary schematic diagram of emission spectra of two fluorescent dyes of a mixed dye used in a sample testing method according to an embodiment of the disclosure.

FIG. 2 shows an exemplary schematic diagram of emission spectra of two fluorescent dyes of a mixed dye used in a sample testing method according to an embodiment of the disclosure. For ease of description, the two fluorescent dyes included in the mixed dye are called a first fluorescent dye and a second fluorescent dye, respectively. As shown in FIG. 2, the emission spectrum of the first fluorescent dye is the emission spectrum 210 shown by a dotted line, and the emission spectrum of the second fluorescent dye is the emission spectrum 220 shown by a solid line.

A peak point of the emission spectrum 210 of the first fluorescent dye is D, and a peak point of the emission spectrum 220 of the second fluorescent dye is A. In one embodiment of the disclosure, a difference between the respective abscissas of the point D and the point A (i.e., a difference between wavelengths $\lambda$ corresponding to the peaks) is greater than 30 nanometers and less than 80 nanometers. In addition, the overlap between the emission spectrum 210 of the first fluorescent dye and the emission spectrum 220 of the second fluorescent dye is a ratio of an area of a first polygon to an area of a second polygon. The area of the first polygon is equal to an area of a curved polygon surrounded by three points E, G and C; and the area of the second polygon is equal to an area of a curved polygon surrounded by the emission spectrum 210 of the first fluorescent dye (or the emission spectrum 220 of the second fluorescent dye) and a base line 230. When a ratio of an overlapping part of the emission spectrum 210 of the first fluorescent dye and the emission spectrum 220 of the second fluorescent dye relative to the emission spectrum 210 of the first fluorescent dye is being calculated, the area of the second polygon is equal to the area of the curved polygon surrounded by the emission spectrum 210 of the first fluorescent dye and the base line 230.

When a ratio of an overlapping part of the emission spectrum 210 of the first fluorescent dye and the emission spectrum 220 of the second fluorescent dye relative to the emission spectrum 220 of the second fluorescent dye is being calculated, the area of the second polygon is equal to the area of the curved polygon surrounded by the emission spectrum 220 of the second fluorescent dye and the base line 230. That is to say, the ratio of the overlapping part of the emission spectrum 210 of the first fluorescent dye and the emission spectrum 220 of the second fluorescent dye relative to each of the respective emission spectra should not be greater than 50%. For the sake of brevity, it is described herein that the overlap between the emission spectrum 210 of the first fluorescent dye and the emission spectrum 220 of the second fluorescent dye is not greater than 50%. The base line 230 is a dotted horizontal line parallel to a horizontal axis as shown in FIG. 2, and the horizontal line is at 5% of a normalized peak of the emission spectrum 210 of the first fluorescent dye and the emission spectrum 220 of the second fluorescent dye. The point E and a point F are a left intersection and a right intersection of the emission spectrum 210 of the first fluorescent dye and the base line 230, respectively. A point B and the point C are a left intersection and a right intersection of the emission spectrum 220 of the second fluorescent dye and the base line 230, respectively. In one embodiment of the disclosure, the overlap between the emission spectrum 210 of the first fluorescent dye and the emission spectrum 220 of the second fluorescent dye is not greater than 50%.

In a further embodiment of the disclosure, in order to detect different particles in a single test under the irradiation by a single light source, the applicant has determined that the absolute value of the difference between the wavelengths corresponding to the peaks of the emission spectra of the two fluorescent dyes included in the aforementioned mixed dye may be, in addition to being in the range of 30 nanometers to 80 nanometers, greater than 40 nanometers and less than 80 nanometers; or greater than 50 nanometers and less than 80 nanometers; or greater than 50 nanometers and less than 70 nanometers. Similarly, the overlap between the emission spectra of the two fluorescent dyes included in the mixed dye described above may be, in addition to being not greater than 50%, not greater than 35%, or even not greater than 15%. Under any combination of the above-mentioned conditions, different particles can be detected in a single test under the irradiation by a single light source, which will be described later in conjunction with specific embodiments.

In one embodiment of the disclosure, at least one of the two fluorescent dyes used in step S120 may be a dye with a large Stokes shift. In one embodiment of the disclosure, the dye with a large Stokes shift may be a dye with a difference between wavelengths corresponding to respective peaks of an emission spectrum and an excitation spectrum thereof that is greater than a predetermined threshold. The following description will be made in conjunction with FIGS. 3 and 4.

Figure 3:
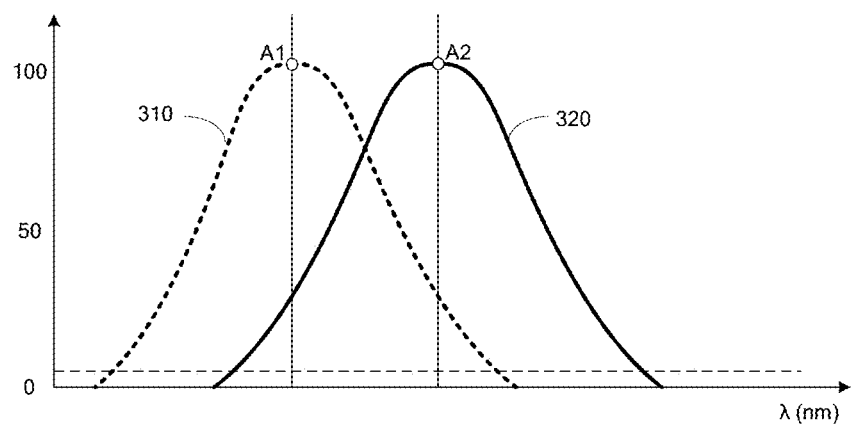
FIG. 3 shows an exemplary schematic diagram of an emission spectrum and an excitation spectrum of one fluorescent dye of a mixed dye used in a sample testing method according to an embodiment of the disclosure.

FIG. 3 shows an exemplary schematic diagram of an emission spectrum and an excitation spectrum of one fluorescent dye of a mixed dye used in a sample testing method according to an embodiment of the disclosure. As shown in FIG. 3, the excitation spectrum (also called absorption spectrum) of the fluorescent dye is the excitation spectrum 310 shown by a dotted line, and the emission spectrum of the fluorescent dye is the emission spectrum 320 shown by a solid line. A peak point of the excitation spectrum 310 is A1, and a peak point of the emission spectrum 320 is A2. In one embodiment of the disclosure, a difference between the respective abscissas of the point A2 and the point A1 (i.e., a difference between wavelengths corresponding to the respective peaks of the emission spectrum and the excitation spectrum) is greater than a predetermined threshold. In an example, the predetermined threshold is 30 nanometers. In another example, the predetermined threshold is 50 nanometers. In yet another example, the difference between respective abscissas of the point A2 and the point A1 (i.e., the difference between wavelengths corresponding to the respective peaks of the emission spectrum and the excitation spectrum) may be greater than 30 nanometers and less than 150 nanometers. In a further example, the difference between the respective abscissas of the point A2 and the point A1 (i.e., the difference between wavelengths corresponding to the respective peaks of the emission spectrum and the excitation spectrum) may be greater than 50 nanometers and less than 100 nanometers.

In an embodiment of the disclosure, the above-described dye with a large Stokes shift, which has the difference between the wavelengths corresponding to the respective peaks of the emission spectrum and the excitation spectrum greater than the predetermined threshold, may be mixed with a common dye (a dye without a large Stokes shift) to form the combined dye used in step S120, or the above-described dye with a large Stokes shift, which has the difference between the wavelengths corresponding to the respective peaks of the emission spectrum and the excitation spectrum greater than the predetermined threshold, may be mixed with another dye with a large Stokes shift to form the combined dye used in step S120. Since the difference between the wavelengths corresponding to the respective peaks of the emission spectrum and the excitation spectrum of a dye with a large Stokes shift is greater than the predetermined threshold, it is advantageous for two fluorescent dyes of the mixed dye including at least one dye with a large Stokes shift to meet the aforementioned conditions about the difference between the wavelengths corresponding to the peaks of the emission spectra and the overlap between the emission spectra, thereby making it easier to detect different particles in a single test under the irradiation by a single light source.

Figure 4:
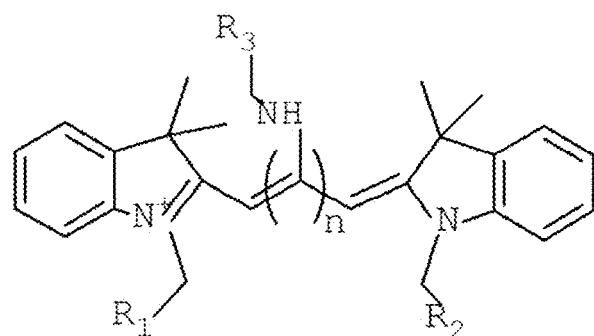
FIG. 4 shows an exemplary schematic diagram of a parent structure of the fluorescent dye shown in FIG. 3.
Figure 6:
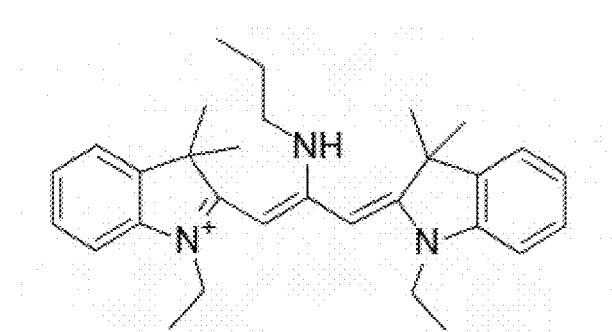
FIGS. 6 and 7 show exemplary schematic diagrams of structures of two dyes of a mixed dye used in a sample testing method according to an embodiment of the disclosure.

In an embodiment of the disclosure, the above-described dye with a large Stokes shift can be used to differentiate white blood cells of a blood sample, and a parent structure of the dye will be described below in conjunction with FIG. 4. FIG. 4 shows an exemplary schematic diagram of a parent structure of the fluorescent dye shown in FIG. 3. As shown in FIG. 4, a parent of the dye with a large Stokes shift may be a meso-amino-substituted cyanine dye (or a dye with another structure). In addition, carbazole, coumarin and other dye parents with a typical electronic push-pull system may be modified as the parent structure, for differentiating white blood cells. In FIG. 4, R1, R2 and R3 are substituent groups, which may be any element. FIG. 6 shows a schematic diagram of a dye structure obtained when they are all hydrogen elements.

Figure 5:
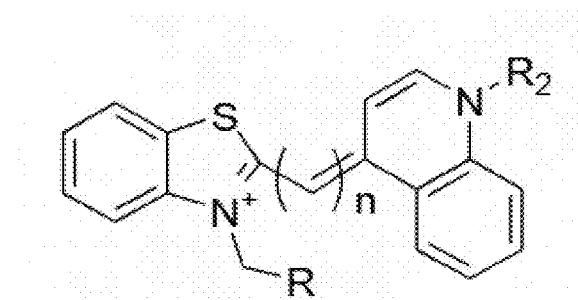
FIG. 5 shows an exemplary schematic diagram of a parent structure of the other fluorescent dye of the mixed dye used in a sample testing method according to an embodiment of the disclosure.
Figure 7:
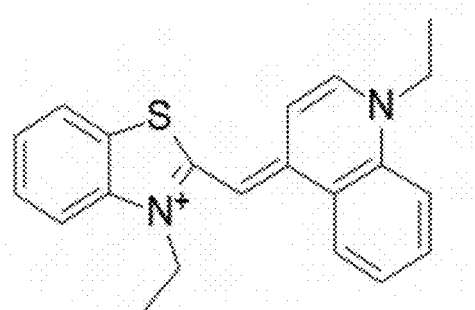

FIG. 5 shows an exemplary schematic diagram of a parent structure of the other fluorescent dye of the mixed dye used in a sample testing method according to an embodiment of the disclosure. As shown in FIG. 5, the fluorescent dye may be a nucleic acid dye, which may be used for detecting red blood cells in a blood sample. In FIGS. 5, R and are substituent groups, which may be any element. FIG. 7 shows a schematic diagram of a dye structure obtained when they are all hydrogen elements.

In an embodiment of the disclosure, the dye with a large Stokes shift shown in FIG. 6 may be mixed with another fluorescent dye shown in FIG. 7 to detect cells in a blood sample. An embodiment in which cells in a blood sample are detected by using a mixed dye including the fluorescent dyes shown in FIGS. 6 and 7 will be described below in conjunction with FIGS. 6 to 13.

In an embodiment, the sample to be tested obtained in step S110 may be a blood sample. The reagent provided in step S120 may include a first reagent and a second reagent. The first reagent includes a first fluorescent dye and a second fluorescent dye (their respective structures may be as shown in FIGS. 6 and 7, respectively). In this embodiment, a difference between wavelengths corresponding to peaks of respective emission spectra of the first fluorescent dye and the second fluorescent dye is equal to 62 nanometers, and the overlap between the emission spectra of the first fluorescent dye and the second fluorescent dye is 31%. In addition, the first reagent may further include a solvent (e.g., ethylene glycol), and the first fluorescent dye and the second fluorescent dye may be prepared in the solvent according to corresponding concentrations to obtain the first reagent. The second reagent may be a hemolytic agent. The first reagent, the second reagent and the blood sample are uniformly mixed and then incubated at a predetermined temperature for a predetermined time to obtain a sample solution to be tested. The sample solution to be tested is flowed in a flow cell in a single test, and light with a single wavelength is used to irradiate the particles flowing in the flow cell, such that the particles generate optical signals, fluorescence signals are detected from the optical signals, and a cell test result of the blood sample is obtained based on the fluorescence signals.

In an example, in the first reagent described above, a concentration of the first fluorescent dye was 0.05 gram/litter (g/L), a concentration of the second fluorescent dye was 0.025 g/L, the solvent is ethylene glycol, and methanol with a concentration of 10 g/L was further included. 4 microliters of blood sample to be tested, 20 microliters of first reagent and 1 microliter of second reagent were provided, and these were uniformly mixed and then incubated at 42° C. for 40 seconds to obtain a sample solution to be tested. The sample solution to be tested was placed in a flow cytometer (Mindray BriCyte E6), and a fluorescein isothiocyanate (FITC) measurement and a peridinin chlorophyll protein (PerCP) measurement were then opened for performing counting. Specifically, a first detection threshold of 500 was set first, and forward-scattered signals and FITC fluorescence signals of blood cell fragments were mainly detected, and a counting of particles detected was 5000. A second detection threshold of 20000 was set, so as to continue to detect side-scattered signals and PerCP fluorescence signals of white blood cells, a counting of particles detected was 2000. Counting diagrams obtained are shown in FIGS. 8 and 9.

Figure 8:
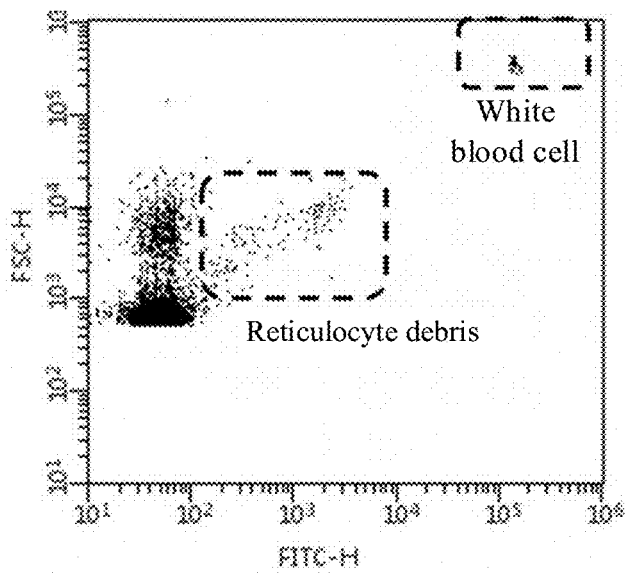
FIGS. 8 and 9 show exemplary schematic diagrams of particle test results obtained by using a sample testing method according to an embodiment of the disclosure.
Figure 9:
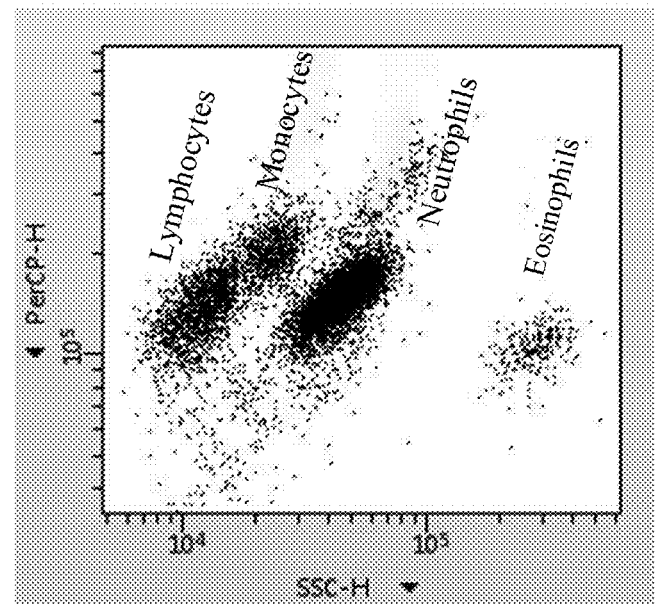

FIG. 8 shows a scatter diagram of particles detected by using FITC measurement, including reticulocyte (RET) fragment particles and white blood cells (WBCs). FIG. 9 shows a scatter diagram of particles detected by using PerCP measurement, including various types of white blood cells. Based on the scatter diagram of FIG. 9, classification and counting results of the white blood cells are as follows: a percentage of lymphocytes is 29.8%; a percentage of monocytes is 5.7%; a percentage of neutrophils is 60.6%; and a percentage of eosinophils is 3.1%. It can be seen therefrom that the sample testing method according to the above embodiment of the disclosure can be used to detect multiple parameters (reticulocyte fragments, white blood cells, etc.) of one blood sample in a single test (in a single reaction channel) under a hemolytic condition; and the detection can be performed by using the white blood cell detection channel of an existing instrument.

The above blood sample is tested on a blood cell analyzer (Mindray BC-6800) and cell test results obtained are as follows: a percentage of reticulocytes is 3.2%; a percentage of lymphocytes is 31.1%; a percentage of monocytes is 5.5%; a percentage of neutrophils is 60%; a percentage of eosinophils is 3.2%; and a percentage of basophils is 0.2%. Through this comparison, it can be seen that the sample testing method according to the above embodiment of the disclosure can be used to accurately classify and count white blood cells in a blood sample.

Figure 10:
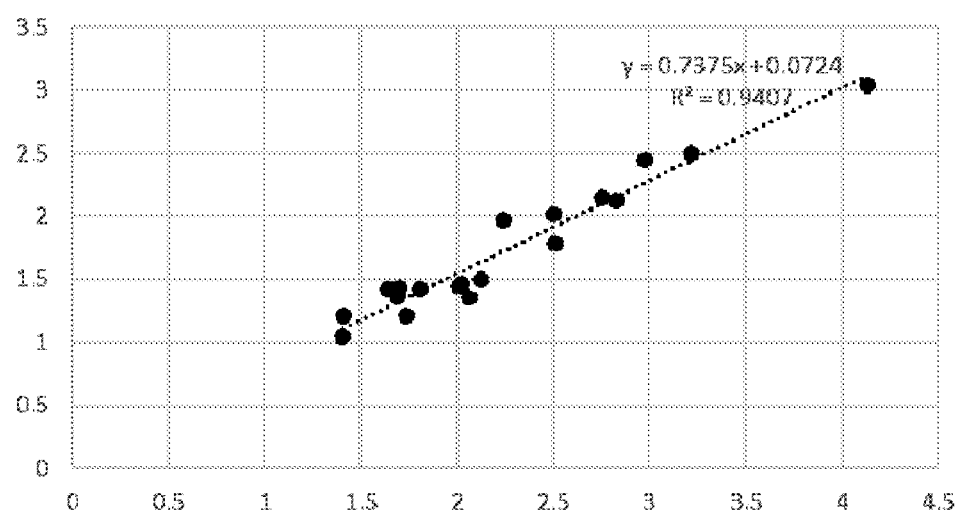
FIG. 10 shows a schematic diagram of a correlation between a percentage of reticulocyte fragment particles detected by using a sample testing method according to an embodiment of the disclosure, and a percentage of reticulocytes tested on a blood cell analyzer.

In addition, in the above embodiment, reticulocytes are treated with a hemolytic agent to form reticulocyte fragment particles, as shown in FIG. 8, in which a small amount of nucleic acid substances can be stained with a dye, such that particles can be exhibited in a fluorescence direction. Based on the number of WBC particles, the percentage of RET particles can be calculated, and its content is 2.5%. Since these RET particles are not complete RET cells, they cannot be counted absolutely. However, this percentage RET particles and a percentage of reticulocytes measured on the blood cell analyzer have a good correlation, as shown in FIG. 10.

In the embodiments described above in conjunction with FIGS. 6 to 10, first fluorescence signals and second fluorescence signals may be detected under a hemolytic condition. The first fluorescence signals may include fluorescence signals that are emitted, under irradiation by a light source, by cells in the blood sample that have been stained with the first fluorescent dye; and the second fluorescence signals may include fluorescence signals that are emitted, under irradiation by the light source, by cells in the blood sample that have been stained with the second fluorescent dye. A classification result and/or a counting result of white blood cells in the blood sample may be obtained based on the first fluorescence signals and scattered light signals, and information about reticulocytes in the blood sample can be obtained based on the second fluorescence signals.

In an embodiment, obtaining information about the reticulocytes in the blood sample may include obtaining a counting result of reticulocyte fragments in the blood sample. The counting result may be obtained based on the second fluorescence signals alone or in combination with the second fluorescence signals and scattered light signals. The scattered light signals may include forward-scattered light signals and/or side-scattered light signals. Combining the second fluorescence signals and the scattered light signals can more accurately distinguish white blood cells from reticulocyte fragments, so that a more accurate counting result of the reticulocyte fragments can be obtained. A proportion of the reticulocytes in all red blood cells in the blood sample can be obtained based on the counting result. For example, the proportion of the reticulocytes in all the red blood cells in the blood sample may be calculated as following: calculating a first ratio, which is a ratio of the counting result of the reticulocyte fragments to the counting result of the white blood cells in the blood sample; calculating a third ratio based on the first ratio and a second ratio measured in advance, wherein the second ratio is a ratio of the counting result of the white blood cells to the counting result of the red blood cells in the blood sample, and the third ratio is a proportion of the reticulocyte fragments in all the red blood cells in the blood sample; and calculating the proportion of the reticulocytes in all the red blood cells in the blood sample based on the third ratio and a preset standard curve, wherein the preset standard curve reflects a relationship between the proportion of the reticulocyte fragments in all the red blood cells and the proportion of the reticulocytes in all the red blood cells.

In an embodiment, obtaining the classification result of the white blood cells in the blood sample may include: classifying the white blood cells in the blood sample as lymphocytes, monocytes, neutrophils, and eosinophils. In an embodiment, obtaining the counting result of the white blood cells in the blood sample may include: counting the white blood cells in the blood sample, or after the white blood cells in the blood sample are classified as lymphocytes, monocytes, neutrophils, and eosinophils, counting the lymphocytes, the monocytes, the neutrophils, and the eosinophils respectively. The classification result and/or the counting result of the white blood cells may be obtained based on the first fluorescence signals and the scattered light signals. In addition, the counting result of the white blood cells may also be obtained based on the second fluorescence signals described above.

Another embodiment in which cells of a blood sample are detected by using a mixed dye including the fluorescent dyes shown in FIGS. 6 and 7 will be described below in conjunction with FIGS. 11 to 13.

In another embodiment, the sample to be tested obtained in step S110 may be a blood sample. The reagent provided in step S120 may include a first reagent and a second reagent. The first reagent includes a first fluorescent dye and a second fluorescent dye (their respective parent structures may be as shown in FIGS. 6 and 7, respectively). In this embodiment, a difference between wavelengths corresponding to peaks of respective emission spectra of the first fluorescent dye and the second fluorescent dye is equal to 62 nanometers, and the overlap between the emission spectra of the first fluorescent dye and the second fluorescent dye is 31%. In addition, the first reagent may further include a solvent (e.g., ethylene glycol), and the first fluorescent dye and the second fluorescent dye may be prepared in the solvent according to corresponding concentrations to obtain the first reagent. The second reagent may be a diluent. The first reagent, the second reagent and the blood sample are uniformly mixed and then incubated at a predetermined temperature for a predetermined time to obtain a sample solution to be tested. The sample solution to be tested are flowed in a flow cell in a single test, light with a single wavelength is used to irradiate the particles flowing in the flow cell, such that the particles generate optical signals, fluorescence signals are detected from the optical signals, and a cell test result of the blood sample is obtained based on the fluorescence signals.

In an example, in the first reagent described above, a concentration of the first fluorescent dye was 0.05 g/L, a concentration of the second fluorescent dye was 0.025 g/L, the solvent is ethylene glycol, and methanol with a concentration of 10 g/L was further included. 4 microliters of blood sample to be tested, 20 microliters of first reagent and 1 microliter of second reagent were provided, and these were uniformly mixed and then incubated at 42° C. for 40 seconds to obtain a sample solution to be tested. The sample solution to be tested was placed in a flow cytometer (Mindray BriCyte E6), and an FITC measurement and a PerCP measurement were then opened for performing counting. Specifically, a first detection threshold of 500 was set first, and forward-scattered signals and FITC fluorescence signals of blood cell fragments were mainly detected, and a counting of particles detected was 5000. A second detection threshold of 20000 was set, white blood cells were separated from red blood cells by fluorescence signals, and a percentage of each population of white blood cells was calculated respectively. The obtained counting diagrams are shown in FIGS. 11 and 12.

Figure 11:
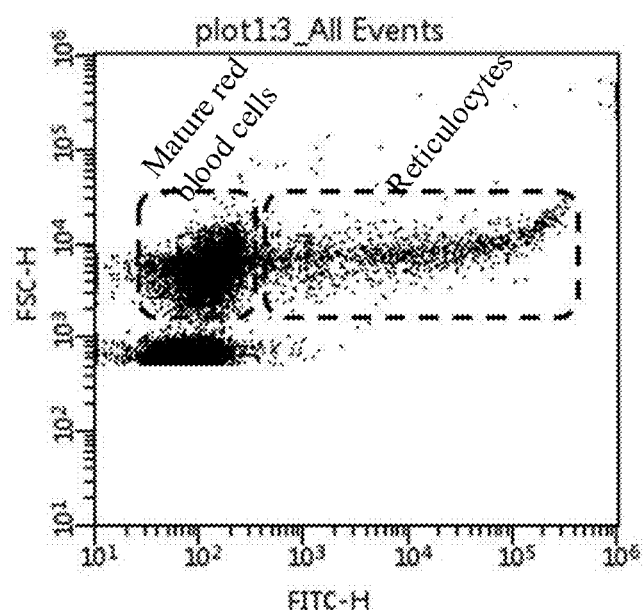
FIGS. 11 and 12 show exemplary schematic diagrams of particle test results obtained by using a sample testing method according to another embodiment of the disclosure.
Figure 12:
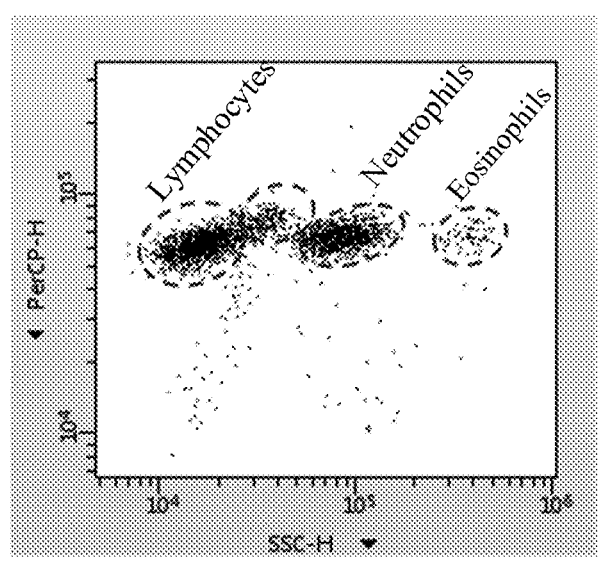

FIG. 11 shows a scatter diagram of particles detected by using FITC measurement, including mature red blood cells and reticulocytes. FIG. 12 shows a scatter diagram of particles detected by using PerCP measurement, including various types of white blood cells. Based on the scatter diagrams of FIGS. 11 and 12, a percentage of the reticulocytes obtained is 5.14%, and classification and counting results of the white blood cells are as follows: a percentage of lymphocytes is 34.9%; a percentage of monocytes is 3.7%; a percentage of neutrophils is 57.8%; and a percentage of eosinophils is 3.6%. It can be seen therefrom that the sample testing method according to the above embodiment of the disclosure can be used to detect multiple parameters (reticulocytes, mature red blood cells, white blood cells, etc.) of a blood sample in a single test (in single reaction channel) under a non-hemolytic condition; and the detection can be performed by using a white blood cell detection channel of an existing instrument.

The above blood sample is tested on a blood cell analyzer (Mindray BC-6800) and cell test results obtained are as follows: a percentage of reticulocytes is 4.98%; a percentage of lymphocytes is 34.5%; a percentage of monocytes is 3.6%; a percentage of neutrophils is 58.0%; a percentage of eosinophils is 3.4%; and a percentage of basophils is 0.5%.

Through this comparison, it can be seen that in the sample testing method according to the above embodiment of the disclosure, in a single test under a non-hemolytic condition, reticulocytes and white blood cells are counted simultaneously, and different types of white blood cells can be effectively distinguished at the same time; and the detection can be performed by using an existing RET channel of an existing instrument.

Figure 13:
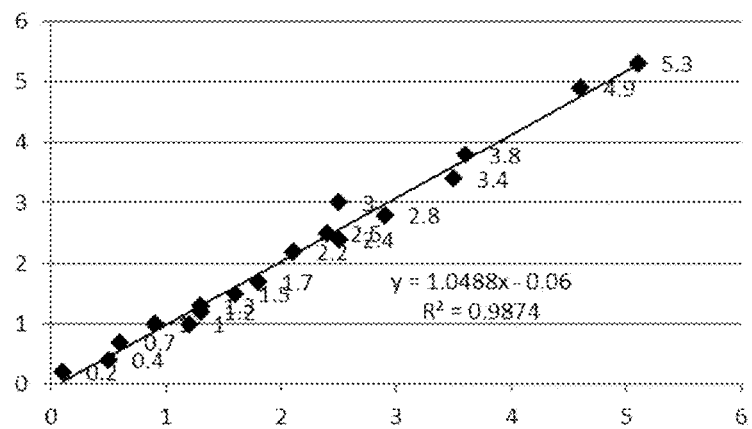
FIG. 13 shows a schematic diagram of a correlation between a percentage of reticulocytes detected by using a sample testing method according to an embodiment of the disclosure, and a percentage of reticulocytes tested on a blood cell analyzer.

FIG. 13 shows a schematic diagram of a correlation between a percentage of reticulocytes detected by using a sample testing method according to an embodiment of the disclosure, and a percentage of reticulocytes tested on a blood cell analyzer. It can be seen from FIG. 13 that the percentage of reticulocytes detected by using the sample testing method according to the embodiment of the disclosure has a good correlation with the percentage of reticulocytes tested by the blood cell analyzer, which shows that the sample testing method according to the embodiment of the disclosure has a good accuracy when used for testing the percentage of the reticulocytes.

In the embodiments described above in conjunction with FIGS. 11 to 13, first fluorescence signals and second fluorescence signals can be detected under a non-hemolytic condition. The first fluorescence signals may include fluorescence signals that are emitted, under irradiation by a light source, by cells in the blood sample that have been stained with the first fluorescent dye; and the second fluorescence signals may include fluorescence signals that are emitted, under irradiation by the light source, by cells in the blood sample that have been stained with the second fluorescent dye. A classification result and/or a counting result of white blood cells in the blood sample are obtained based on the first fluorescence signals, and a classification result and/or a counting result of red blood cells in the blood sample are obtained based on the second fluorescence signals.

In an embodiment, obtaining a classification result and/or a counting result of red blood cells in the blood sample based on the second fluorescence signals may further include: obtaining a counting result of reticulocytes in the blood sample based on the second fluorescence signals; or obtaining a classification result and/or a counting result of red blood cells in the blood sample based on the second fluorescence signals and scattered light signals. In an embodiment, obtaining the classification result of the red blood cells in the blood sample may include: classifying the red blood cells in the blood sample as mature red blood cells and reticulocytes. In an embodiment, obtaining the counting result of the red blood cells in the blood sample may include: counting the red blood cells in the blood sample, or after the red blood cells in the blood sample are classified as mature red blood cells and reticulocytes, counting the mature red blood cells and the reticulocytes respectively. Combining the second fluorescence signal and the scattered light signals can more accurately distinguish white blood cells, reticulocytes, and mature red blood cells from one another, so that more accurate classification and counting results of the red blood cells can be obtained.

In an embodiment, obtaining the classification result of the white blood cells in the blood sample may include: classifying the white blood cells in the blood sample as lymphocytes, monocytes, neutrophils, and eosinophils. In an embodiment, obtaining the counting result of the white blood cells in the blood sample may include: counting the white blood cells in the blood sample, or after the white blood cells in the blood sample are classified as lymphocytes, monocytes, neutrophils, and eosinophils, counting the lymphocytes, the monocytes, the neutrophils, and the eosinophils respectively. The classification result and/or the counting result of the white blood cells may be obtained based on the first fluorescence signal and the scattered light signals. In addition, the counting result of the white blood cells may also be obtained based on the second fluorescence signals described above.

The above embodiments describe a scene in which multiple parameters of one blood sample are detected in a single test by using a mixed dye including two fluorescent dyes in the sample testing method according to the embodiments of the disclosure. In a further embodiment of the disclosure, the sample testing method according to the embodiment of the disclosure may also use a mixed dye including more than two dyes to detect multiple parameters of one blood sample in a single test.

That is, the reagent further comprises a third fluorescent dye, the fluorescence signals further comprise third fluorescence signals, and obtaining a particle test result of the sample to be tested based on at least the fluorescence signals further comprises: obtaining the third particle test result of the sample to be tested based on at least the third fluorescence signals.

In an embodiment, obtaining a third particle test result of the sample to be tested based on at least the third fluorescence signals further comprises: obtaining the third particle test result of the sample to be tested based on the third fluorescence signals and the scattered light signals.

The following will be described with reference to FIGS. 14 to 20 by taking three fluorescent dyes as an example.

Figure 14:
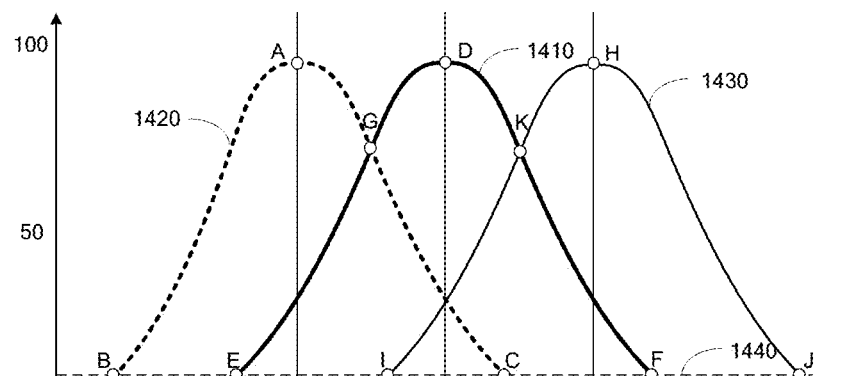
FIG. 14 shows an exemplary schematic diagram of emission spectra of three fluorescent dyes of a mixed dye used in a sample testing method according to an embodiment of the disclosure.

FIG. 14 shows an exemplary schematic diagram of emission spectra of three fluorescent dyes of a mixed dye used in a sample testing method according to an embodiment of the disclosure. For ease of description, the three fluorescent dyes included in the mixed dye are called a first fluorescent dye, a second fluorescent dye and a third fluorescent dye, respectively. As shown in FIG. 14, the emission spectrum of the first fluorescent dye is the emission spectrum 1410 shown by a dotted line, the emission spectrum of the second fluorescent dye is the emission spectrum 1420 shown by a solid line, and the emission spectrum of the third fluorescent dye is the emission spectrum 1430 shown by a solid line.

A peak point of the emission spectrum 1410 of the first fluorescent dye is D, a peak point of the emission spectrum 1420 of the second fluorescent dye is A, and a peak point of the emission spectrum 1430 of the third fluorescent dye is H. In one embodiment of the disclosure, a difference between the respective abscissas of the point D and the point A (i.e., a difference between wavelengths corresponding to the peaks) is greater than 30 nanometers and less than 80 nanometers, and a difference between the respective abscissas of the point H and the point D (i.e., a difference between wavelengths corresponding to the peaks) is greater than 30 nanometers and less than 80 nanometers. That is, a difference between the wavelengths corresponding to the peaks of the emission spectra of the first fluorescent dye and the second fluorescent dye is greater than 30 nanometers and less than 80 nanometers, and a difference between the wavelengths corresponding to the peaks of the emission spectra of the third fluorescent dye and the first fluorescent dye is greater than 30 nanometers and less than 80 nanometers.

In addition, the overlap between the emission spectrum 1410 of the first fluorescent dye and the emission spectrum 1420 of the second fluorescent dye is a ratio of an area of a first polygon to an area of a second polygon. The area of the first polygon is equal to an area of a curved polygon surrounded by three points E, G and C; and the area of the second polygon is equal to an area of a curved polygon surrounded by the emission spectrum 1410 of the first fluorescent dye (or the emission spectrum 1420 of the second fluorescent dye) and a base line 1440. The base line 1440 is a dotted horizontal line parallel to a horizontal axis as shown in FIG. 14, and the horizontal line is at 5% of a normalized peak height of the emission spectra of the first fluorescent dye, the second fluorescent dye and the third fluorescent dye. The point E and a point F are a left intersection and a right intersection of the emission spectrum 1410 of the first fluorescent dye and the base line 1440, respectively. A point B and the point C are a left intersection and a right intersection of the emission spectrum 1420 of the second fluorescent dye and the base line 1440, respectively. In one embodiment of the disclosure, the overlap between the emission spectrum 1410 of the first fluorescent dye and the emission spectrum 1420 of the second fluorescent dye is not greater than 50%.

In addition, the overlap between the emission spectrum 1410 of the first fluorescent dye and the emission spectrum 1430 of the third fluorescent dye is a ratio of an area of a third polygon to an area of a fourth polygon. The area of the third polygon is equal to an area of a curved polygon surrounded by three points I, K and F; and the area of the fourth polygon is equal to an area of a curved polygon surrounded by the emission spectrum 1410 of the first fluorescent dye (or the emission spectrum 1430 of the third fluorescent dye) and the base line 1440. The point I and a point J are a left intersection and a right intersection of the emission spectrum 1430 and the base line 1440 of the third fluorescent dye, respectively. In one embodiment of the disclosure, the overlap between the emission spectrum 1420 of the first fluorescent dye and the emission spectrum 1430 of the third fluorescent dye is not greater than 50%.

In this embodiment, since, among the three fluorescent dyes, a difference between wavelengths corresponding to peaks of emission spectra of the first fluorescent dye and the second fluorescent dye and an overlap between the emission spectra of the two fluorescent dyes are each within a preset range, and a difference between wavelengths corresponding to peaks of emission spectra of the third fluorescent dye and the first fluorescent dye and an overlap between the emission spectra of the two fluorescent dyes are each within a preset range, different cells in the blood sample are stained by the different dyes of the mixed dye including the three fluorescent dyes and then irradiated by the same light source, and different fluorescence signals are then emitted, so that multiple parameters of one blood sample can be detected in a single test (in a single reaction channel).

Figure 15:
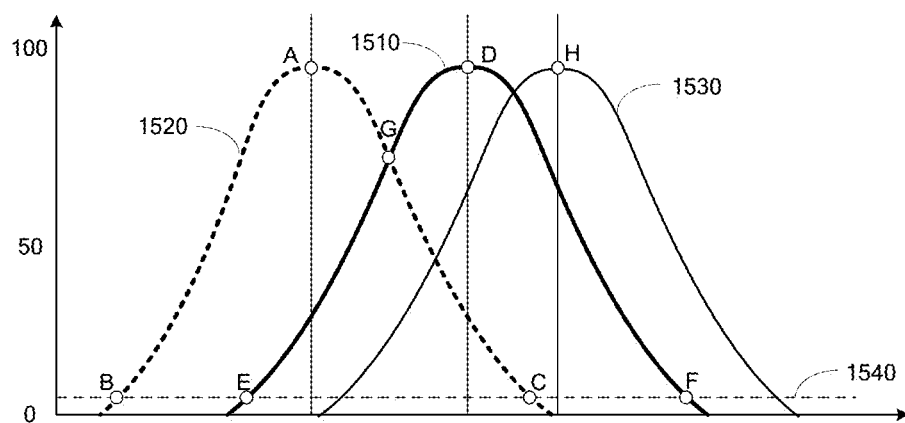
FIG. 15 shows an exemplary schematic diagram of emission spectra of three fluorescent dyes of a mixed dye used in a sample testing method according to another embodiment of the disclosure.

FIG. 15 shows an exemplary schematic diagram of emission spectra of three fluorescent dyes of a mixed dye used in a sample testing method according to another embodiment of the disclosure. For ease of description, the three fluorescent dyes included in the mixed dye are called a first fluorescent dye, a second fluorescent dye and a third fluorescent dye, respectively. As shown in FIG. 15, the emission spectrum of the first fluorescent dye is the emission spectrum 1510 shown by a dotted line, the emission spectrum of the second fluorescent dye is the emission spectrum 1520 shown by a solid line, and the emission spectrum of the third fluorescent dye is the emission spectrum 1530 shown by a solid line.

A peak point of the emission spectrum 1510 of the first fluorescent dye is D, a peak point of the emission spectrum 1520 of the second fluorescent dye is A, and a peak point of the emission spectrum 1530 of the third fluorescent dye is H. In one embodiment of the disclosure, a difference between the respective abscissas of the point D and the point A (i.e., a difference between wavelengths corresponding to the peaks) is greater than 30 nanometers and less than 80 nanometers, and the abscissa of the point H is greater than that of the point D. That is, a difference between the wavelengths corresponding to the peaks of the emission spectra of the first fluorescent dye and the second fluorescent dye is greater than 30 nanometers and less than 80 nanometers, and the wavelength corresponding to the peak of the emission spectrum 1530 of the third fluorescent dye is greater than the wavelength corresponding to the peak of the emission spectrum of the first fluorescent dye 1510.

In addition, the overlap between the emission spectrum 1510 of the first fluorescent dye and the emission spectrum 1520 of the second fluorescent dye is a ratio of an area of a first polygon to an area of a second polygon. The area of the first polygon is equal to an area of a curved polygon surrounded by three points E, G and C; and the area of the second polygon is equal to an area of a curved polygon surrounded by the emission spectrum 1510 of the first fluorescent dye (or the emission spectrum 1520 of the second fluorescent dye) and a base line 1540. The base line 1540 is a dotted horizontal line parallel to a horizontal axis as shown in FIG. 15, and the horizontal line is at 5% of a normalized peak height of the emission spectra of the first fluorescent dye, the second fluorescent dye and the third fluorescent dye. The point E and a point F are a left intersection and a right intersection of the emission spectrum 1510 of the first fluorescent dye and the base line 1540, respectively. A point B and the point C are a left intersection and a right intersection of the emission spectrum 1520 of the second fluorescent dye and the base line 1540, respectively. In one embodiment of the disclosure, the overlap between the emission spectrum 1510 of the first fluorescent dye and the emission spectrum 1520 of the second fluorescent dye is not greater than 50%.

In this embodiment, since, among the three fluorescent dyes, a difference between wavelengths corresponding to peaks of emission spectra of the first fluorescent dye and the second fluorescent dye and an overlap between the emission spectra of the two fluorescent dyes are each within a preset range, and the wavelength corresponding to the peak of the third fluorescent dye is greater than the wavelength corresponding to the peak of the emission spectrum of the first fluorescent dye, it is possible to make particles in the blood sample that are stained with the first fluorescent dye and the second fluorescent dye emit first fluorescence signals and second fluorescence signals under the irradiation by the same light source (light with the same wavelength), and to make particles in the blood sample that are stained with the third fluorescent dye emit third fluorescence signals under the irradiation by another light source (light with another wavelength), so that multiple parameters of one blood sample are detected in a single test.

Figure 16:
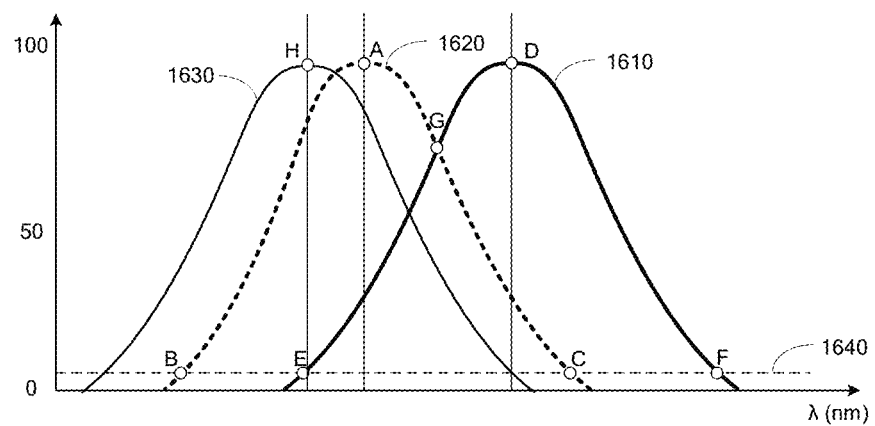
FIG. 16 shows an exemplary schematic diagram of emission spectra of three fluorescent dyes of a mixed dye used in a sample testing method according to a further embodiment of the disclosure.
Figure 17:
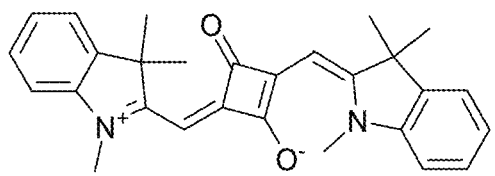
FIG. 17 shows an exemplary schematic diagram of a structure of a third fluorescent dye of a mixed dye used in a sample testing method according to an embodiment of the disclosure.

FIG. 16 shows an exemplary schematic diagram of emission spectra of three fluorescent dyes of a mixed dye used in a sample testing method according to a further embodiment of the disclosure. For ease of description, the three fluorescent dyes included in the mixed dye are called a first fluorescent dye, a second fluorescent dye and a third fluorescent dye, respectively. As shown in FIG. 16, the emission spectrum of the first fluorescent dye is the emission spectrum 1610 shown by a dotted line, the emission spectrum of the second fluorescent dye is the emission spectrum 1620 shown by a solid line, and the emission spectrum of the third fluorescent dye is the emission spectrum 1630 shown by a solid line.

A peak point of the emission spectrum 1610 of the first fluorescent dye is D, a peak point of the emission spectrum 1620 of the second fluorescent dye is A, and a peak point of the emission spectrum 1630 of the third fluorescent dye is H. In one embodiment of the disclosure, a difference between the respective abscissas of the point D and the point A (i.e., a difference between wavelengths corresponding to the peaks) is greater than 30 nanometers and less than 80 nanometers, and the abscissa of the point H is less than that of the point A. That is, a difference between the wavelengths corresponding to the peaks of the emission spectra of the first fluorescent dye and the second fluorescent dye is greater than 30 nanometers and less than 80 nanometers, and the wavelength corresponding to the peak of the emission spectrum 1630 of the third fluorescent dye is less than the wavelength corresponding to the peak of the emission spectrum of the second fluorescent dye 1620.

In addition, the overlap between the emission spectrum 1610 of the first fluorescent dye and the emission spectrum 1620 of the second fluorescent dye is a ratio of an area of a first polygon to an area of a second polygon. The area of the first polygon is equal to an area of a curved polygon surrounded by three points E, G and C; and the area of the second polygon is equal to an area of a curved polygon surrounded by the emission spectrum 1610 of the first fluorescent dye (or the emission spectrum 1620 of the second fluorescent dye) and a base line 1640. The base line 1640 is a dotted horizontal line parallel to a horizontal axis as shown in FIG. 16, and the horizontal line is at 5% of a normalized peak height of the emission spectra of the first fluorescent dye, the second fluorescent dye and the third fluorescent dye. The point E and a point F are a left intersection and a right intersection of the emission spectrum 1610 of the first fluorescent dye and the base line 1640, respectively. A point B and the point C are a left intersection and a right intersection of the emission spectrum 1620 of the second fluorescent dye and the base line 1640, respectively. In one embodiment of the disclosure, the overlap between the emission spectrum 1610 of the first fluorescent dye and the emission spectrum 1620 of the second fluorescent dye is not greater than 50%.

In this embodiment, since, among the three fluorescent dyes, a difference between wavelengths corresponding to peaks of emission spectra of the first fluorescent dye and the second fluorescent dye and an overlap between the emission spectra of the two fluorescent dyes are each within a preset range, and the wavelength corresponding to the peak of the emission spectrum 1630 of the third fluorescent dye is less than the wavelength corresponding to the peak of the emission spectrum 1620 of the second fluorescent dye, it is possible to make particles in the blood sample that are stained with the first fluorescent dye and the second fluorescent dye emit first fluorescence signals and second fluorescence signals under the irradiation by the same light source (light with the same wavelength), and to make particles in the blood sample that are stained with the third fluorescent dye emit third fluorescence signals under the irradiation by another light source (light with another wavelength), so that multiple parameters of one blood sample are detected in a single test.

An embodiment in which cells in a blood sample are detected by using a mixed dye including the fluorescent dyes shown in FIGS. 15 and 16 will be described below with reference to FIGS. 17 to 20.

In this embodiment, the sample to be tested obtained in step S110 may be a blood sample. The reagent provided in step S120 may include a first reagent and a second reagent. The first reagent includes a first fluorescent dye, a second fluorescent dye and a third fluorescent dye (their respective structures may be shown in FIGS. 6, 7 and 17, respectively). In this embodiment, a difference between wavelengths corresponding to peaks of respective emission spectra of the first fluorescent dye and the second fluorescent dye is equal to 62 nanometers, an overlap between the emission spectra of the first fluorescent dye and the second fluorescent dye is 31%, and the wavelength corresponding to the peak of the emission spectrum of the third fluorescent dye is greater than the wavelength corresponding to the peak of the emission spectrum of the second fluorescent dye. In addition, the first reagent may further include a solvent (e.g., ethylene glycol), and the first fluorescent dye, the second fluorescent dye and the third fluorescent dye may be prepared in the solvent according to corresponding concentrations to obtain the first reagent. The second reagent may be a hemolytic agent. The first reagent, the second reagent and the blood sample are uniformly mixed and then incubated at a predetermined temperature for a predetermined time to obtain a sample solution to be tested. The sample solution to be tested are flowed in a flow cell in a single test, light with two wavelengths is used to irradiate the particles flowing in the flow cell, such that the particles generate optical signals, fluorescence signals are detected from the optical signals, and a cell test result of the blood sample is obtained based on the fluorescence signals.

Figure 19:
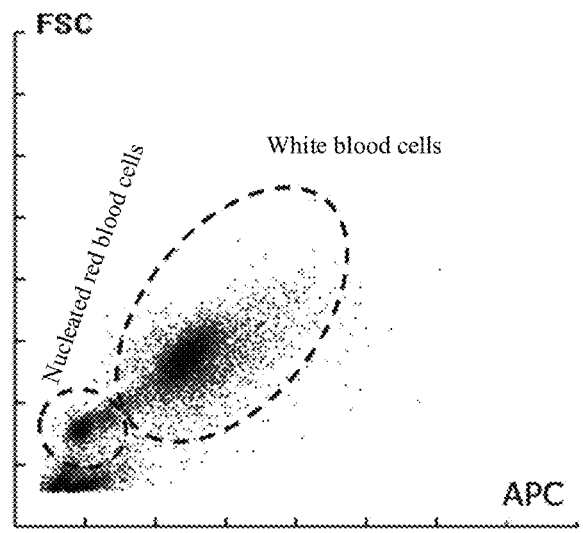
Figure 20:
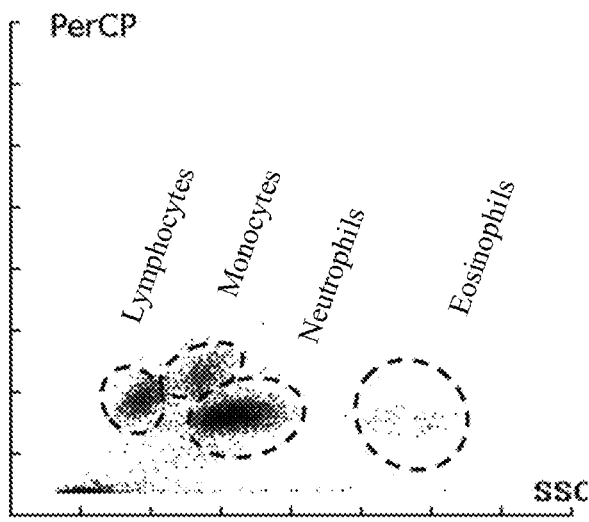

In an example, in the first reagent, a concentration of the first fluorescent dye was 0.05 g/L, a concentration of the second fluorescent dye was 0.025 g/L, a concentration of the third fluorescent dye was 0.025 g/L, the solvent was ethylene glycol, and methanol with a concentration of 10 g/L was further included. 4 microliters of blood sample to be tested, 20 microliters of first reagent and 1 microliter of second reagent were provided, and these were uniformly mixed and then incubated at 42° C. for 40 seconds to obtain a sample solution to be tested. The sample solution to be tested was placed in a flow cytometer (Mindray BriCyte E6), and an FITC measurement (excitation light of 488 nm), a PerCP measurement (excitation light of 488 nm) and an allophycocyanin (APC) measurement (excitation light of 633 nm) were then opened for performing counting. Fluorescence signals collected from the three measurements were emitted fluorescence signals that correspond to the second fluorescent dye, the first fluorescent dye and the third fluorescent dye, respectively. Specifically, a detection threshold was set to 500 first, to mainly collect forward-scattered signals and FITC fluorescence signals of blood cell fragments (signals of reticulocyte fragments in the ghost region). After 5000 particles were collected, the threshold was set to 20000, so as to continue to collect side-scattered signals of white blood cells, PerCP fluorescence signals (signals for differentiating white blood cells) and APC fluorescence signals (signals for differentiating nucleated red blood cells), 2000 particles were collected. The obtained counting diagrams are shown in FIGS. 18 to 20.

Figure 18:
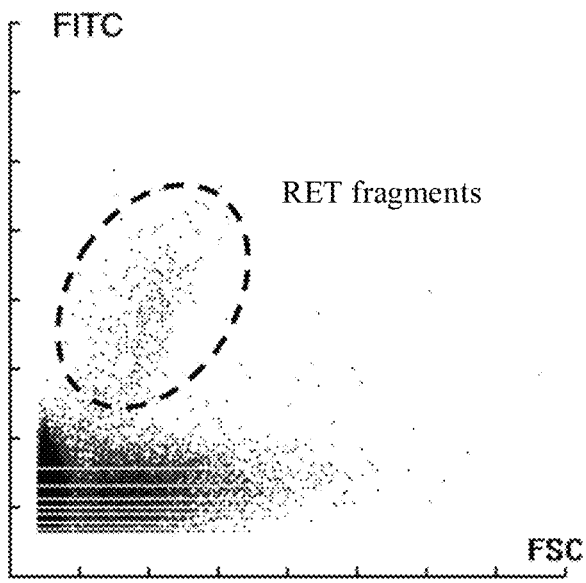
FIGS. 18, 19 and 20 show exemplary schematic diagrams of particle test results obtained by using a sample testing method according to a further embodiment of the disclosure.

FIG. 18 shows a scatter diagram of particles detected by using FITC measurement, including reticulocyte fragments. FIG. 19 shows a scatter diagram of particles detected by using APC measurement, including nucleated red blood cells and white blood cells. FIG. 20 shows a scatter diagram of particles detected by using PerCP measurement, including various types of white blood cells.

Based on the scatter diagram of FIG. 20, classification and counting results of white blood cells are as follows: a percentage of lymphocytes is 23.5%; a percentage of monocytes is 6.4%; a percentage of neutrophils is 68.9%; and a percentage of eosinophils is 1.2%. Based on the scatter diagram of FIG. 19, it can be seen that nucleated red blood cells can be effectively exhibited in the fluorescence direction. By dividing the scatter diagram of the white blood cells in FIG. 19, it can be obtained that the percentage of nucleated red blood cells is 2%. Based on the scatter diagram of FIG. 18, a counting result of reticulocyte fragments can be obtained. It can be seen therefrom that the sample testing method according to the above embodiment of the disclosure can be used to detect multiple parameters (reticulocyte fragments, nucleated red blood cells, white blood cells, etc.) of one blood sample in a single test (in a single reaction channel) under a hemolytic condition.

The above blood sample is tested on a blood cell analyzer (Mindray BC-6800) and cell test results obtained are as follows: a percentage of reticulocytes is 2.2%; a percentage of lymphocytes is 23.2%; a percentage of monocytes is 6.5%; a percentage of neutrophils is 68%; a percentage of eosinophils is 1.1%; or a percentage of basophils is 2.1%. Through this comparison, it can be seen that in the sample testing method according to the above embodiment of the disclosure, three kinds of signals can be collected simultaneously through excitation by two kinds of excitation light, so as to classify and count white blood cells, nucleated red blood cells and reticulocyte fragments.

In the embodiments described above with reference to FIGS. 17 to 20, first fluorescence signals, second fluorescence signals and third fluorescence signals may be detected under a hemolytic condition. The first fluorescence signals may include fluorescence signals that are emitted, under irradiation by a first light source, by cells in the blood sample that have been stained with the first fluorescent dye; the second fluorescence signals may include fluorescence signals that are emitted, under irradiation by the first light source, by cells in the blood sample that have been stained with the second fluorescent dye; and the third fluorescence signals may include fluorescence signals that are emitted, under irradiation by a second light source, by cells in the blood sample that have been stained with the third fluorescent dye. A classification result and/or a counting result of white blood cells in the blood sample are obtained based on the first fluorescence signals and scattered light signals, information about reticulocytes in the blood sample is obtained based on the second fluorescence signals, and a counting result of nucleated red blood cells in the blood sample is obtained based on the third fluorescence signals and the scattered light signals.

In an embodiment, obtaining the information about the reticulocytes in the blood sample may include obtaining a counting result of reticulocyte fragments in the blood sample. The counting result may be obtained based on the second fluorescence signals alone or in combination with the second fluorescence signals and the scattered light signals. The scattered light signals may include forward-scattered light signals and/or side-scattered light signals. Combining the second fluorescence signals and the scattered light signals can more accurately distinguish white blood cells from reticulocyte fragments, so that a more accurate counting result of the reticulocyte fragments can be obtained. A proportion of the reticulocytes in all red blood cells in the blood sample can be obtained based on the counting result. For example, the proportion of the reticulocytes in all the red blood cells in the blood sample may be calculated as following: calculating a first ratio, which is a ratio of the counting result of the reticulocyte fragments to the counting result of the white blood cells in the blood sample; calculating a third ratio based on the first ratio and a second ratio measured in advance, wherein the second ratio is a ratio of the counting result of the white blood cells to the counting result of the red blood cells in the blood sample, and the third ratio is the proportion of the reticulocyte fragments in all the red blood cells in the blood sample; and calculating the proportion of the reticulocytes in all the red blood cells in the blood sample based on the third ratio and a preset standard curve, wherein the preset standard curve reflects a relationship between the proportion of the reticulocyte fragments in all the red blood cells and the proportion of the reticulocytes in all the red blood cells. In an embodiment, obtaining the classification result of the white blood cells in the blood sample may include: classifying the white blood cells in the blood sample as lymphocytes, monocytes, neutrophils, and eosinophils. In an embodiment, obtaining the counting result of the white blood cells in the blood sample may include: counting the white blood cells in the blood sample, or after the white blood cells in the blood sample are classified as lymphocytes, monocytes, neutrophils, and eosinophils, counting the lymphocytes, the monocytes, the neutrophils, and the eosinophils respectively. The classification result and/or the counting result of the white blood cells may be based on the first fluorescence signals and the scattered light signals.

In addition, the counting result of the white blood cells may also be obtained based on the second fluorescence signals described above. In addition, the counting result of the white blood cells may also be obtained based on the third fluorescence signals described above. In addition, the white blood cells and the nucleated red blood cells may be distinguished from each other based on the third fluorescence signals and the scattered light signals described above.

In addition, it is also possible to obtain the proportion of the nucleated red blood cells in all red blood cells in the blood sample based on the counting result of the nucleated red blood cells in the blood sample.

The sample testing method according to the embodiments of the disclosure is exemplarily described above. Based on the above description, according to the sample testing method of the embodiments of the disclosure, a mixed dye including at least two fluorescent dyes is used for performing particle detection on a sample to be tested. Since a difference between wavelengths corresponding to peaks of emission spectra of the two fluorescent dyes and an overlap between the emission spectra of the two fluorescent dyes each within a preset range, different cells in the sample to be tested are stained by the different dyes of the mixed dye and then irradiated by a light source, and different fluorescence signals are then emitted, so that multiple parameters of one sample to be tested can be detected in a single test (in a single reaction channel).

Figure 21:
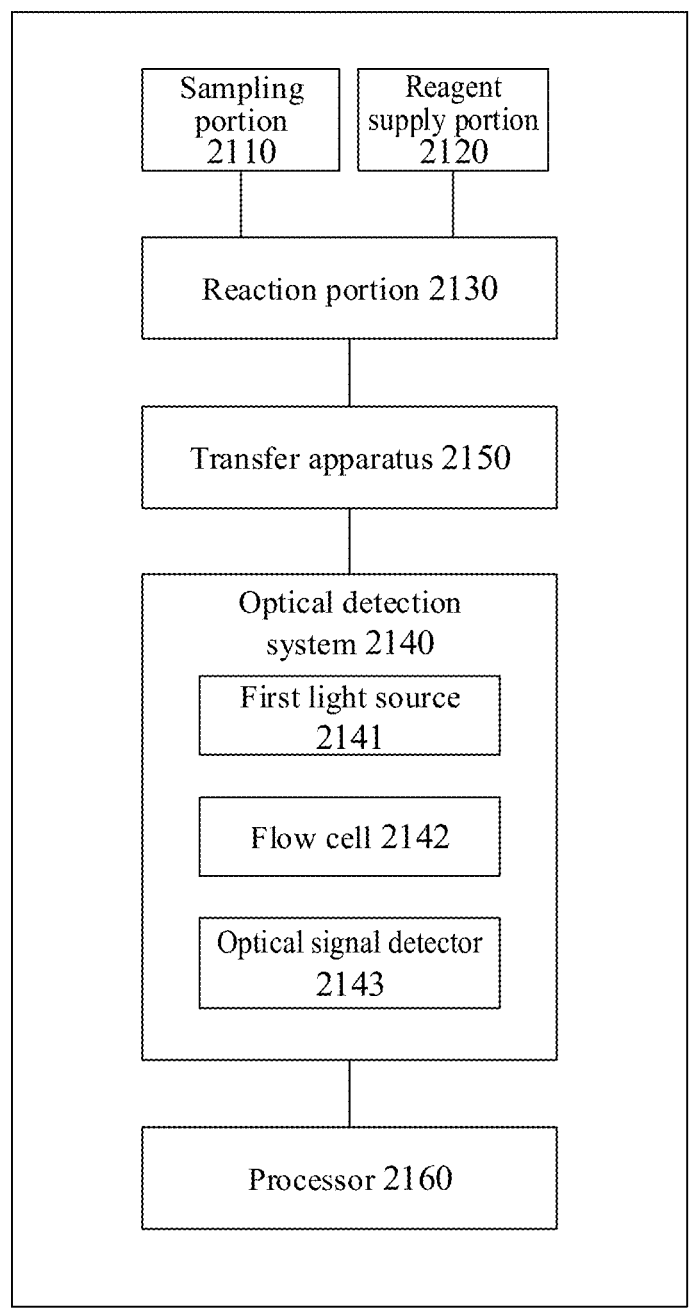
FIG. 21 shows a schematic structural block diagram of a sample analyzer according to an embodiment of the disclosure.

A sample analyzer provided according to another aspect of the disclosure will be described below with reference to FIG. 21. FIG. 21 shows a schematic block diagram of a sample analyzer 2100 according to an embodiment of the disclosure. As shown in FIG. 21, the sample analyzer 2100 includes: a sampling portion 2110 configured to obtain a sample to be tested and transfer the sample to be tested to a reaction portion 2130; a reagent supply portion 2120 configured to store a reagent and supply the reagent to the reaction portion 2130 as required, wherein the reagent includes at least two fluorescent dyes for staining particles in the sample to be tested, wherein an absolute value of a difference between wavelengths corresponding to peaks of emission spectra of the two fluorescent dyes is greater than 30 nanometers and less than 80 nanometers, and an overlap between the emission spectra of the two fluorescent dyes is not greater than 50%; the reaction portion 2130 including a mixing chamber and being configured to mix the sample to be tested and the reagent for reaction to form a sample solution to be tested; an optical detection system 2140, including a first light source 2141, a flow cell 2142 and an optical signal detector 2143, wherein the particles in the sample solution to be tested are capable of flowing in the flow cell 2142 in a single test, the first light source 2141 is configured to irradiate the particles flowing in the flow cell 2142 with a single wavelength such that the particles generate optical signals, and the optical signal detector 2143 is configured to detect at least fluorescence signals from the optical signals; a transfer apparatus 2150 configured to transfer the sample solution to be tested that has been treated with the reagent in the reaction portion 2130, to the flow cell 2142 of the optical detection system 2140; and a processor 2160 configured to obtain a particle test result of the sample to be tested based on at least the fluorescence signals. The sample analyzer 2100 may be configured to execute the sample testing method according to the embodiments of the disclosure described above. Those skilled in the art can understand the structure and operation of the sample analyzer 2100 with reference to the foregoing description of the sample testing method according to the embodiments of the disclosure. For the sake of brevity, specific detailed operations of each component of the sample analyzer 2100 will not be repeated herein, and only their main operating steps will be briefly described.

In an embodiment of the disclosure, the optical signal detector 2143 includes a first fluorescence detector and a second fluorescence detector (not shown). The first fluorescence detector is configured to detect first fluorescence signals from the optical signals, the second fluorescence detector is configured to detect second fluorescence signals from the optical signals, and the processor 2160 is further configured to obtain a first particle test result of the sample to be tested based on at least the first fluorescence signals, and obtain a second particle test result of the sample to be tested based on at least the second fluorescence signals.

In an embodiment of the disclosure, the optical signal detector 2143 further includes scattered light signal detector (not shown). The scattered light signal detector is configured to detect scattered light signals from the optical signals, and the processor 2160 is further configured to obtain the first particle test result of the sample to be tested based on the first fluorescence signals and the scattered light signals.

In an embodiment of the disclosure, the processor 2160 is further configured to obtain the second particle test result of the sample to be tested based on the second fluorescence signals and the scattered light signals.

In an embodiment of the disclosure, the absolute value of the difference between the wavelengths corresponding to the peaks of the emission spectra of the two fluorescent dyes meets any of the following conditions: greater than 40 nanometers and less than 80 nanometers; greater than 50 nanometers and less than 80 nanometers; and greater than 50 nanometers and less than 70 nanometers.

In an embodiment of the disclosure, the overlap between the emission spectra of the two fluorescent dyes is not greater than 35%.

In an embodiment of the disclosure, the overlap between the emission spectra of the two fluorescent dyes is not greater than 15%.

In an embodiment of the disclosure, a difference between wavelengths corresponding to respective peaks of an emission spectrum and an excitation spectrum of at least one of the two fluorescent dyes is greater than a predetermined threshold.

In an embodiment of the disclosure, the reagent further includes a hemolytic agent; and the first particle test result includes a classification result and/or a counting result of white blood cells, and the second particle test result includes information about reticulocytes.

In an embodiment of the disclosure, the information about the reticulocytes includes a counting result of reticulocyte fragments.

In an embodiment of the disclosure, the processor 2160 is further configured to: obtain a proportion of the reticulocytes in all red blood cells in the sample to be tested based on the counting result of the reticulocyte fragments in the sample to be tested.

In an embodiment of the disclosure, the reagent further includes a diluent; and the first particle test result includes a classification result and/or a counting result of white blood cells, and the second particle test result includes a counting result of reticulocytes.

In an embodiment of the disclosure, the reagent further includes a diluent; and the first particle test result includes a classification result and/or a counting result of white blood cells, and the second particle test result includes a classification result and/or a counting result of red blood cells.

In an embodiment of the disclosure, the processor 2160 is further configured to, when obtaining the classification result of the red blood cells in the sample to be tested, classify the red blood cells in the sample to be tested as mature red blood cells and reticulocytes. The processor 2160 is further configured to, when obtaining the counting result of the red blood cells in the sample to be tested, count the red blood cells in the sample to be tested, or after the red blood cells in the sample to be tested are classified as mature red blood cells and reticulocytes, count the mature red blood cells and the reticulocytes respectively.

In an embodiment of the disclosure, the scattered light signals include forward-scattered light signals and/or side-scattered light signals.

In an embodiment of the disclosure, the processor 2160 is further configured to, when obtaining the classification result of the white blood cells in the sample to be tested, classify the white blood cells in the sample to be tested as lymphocytes, monocytes, neutrophils, and eosinophils. The processor 2160 is further configured to, when obtaining the counting result of the white blood cells in the sample to be tested, count the white blood cells in the sample to be tested, or after the white blood cells in the sample to be tested are classified as lymphocytes, monocytes, neutrophils, and eosinophils, count the lymphocytes, the monocytes, the neutrophils, and the eosinophils respectively.

In an embodiment of the disclosure, the predetermined threshold is 30 nanometers.

In an embodiment of the disclosure, the difference between the wavelengths corresponding to the respective peaks of the emission spectrum and the excitation spectrum of the at least one of the two fluorescent dyes meets any of the following conditions: greater than 50 nanometers; greater than 30 nanometers and less than 150 nanometers; greater than 50 nanometers and less than 100 nanometers.

In an embodiment of the disclosure, the reagent further includes a third fluorescent dye, and the optical signal detector 2143 further includes a third fluorescence detector (not shown). The third fluorescence detector is configured to detect third fluorescence signals from the optical signals, and the processor 3260 may be further configured to obtain a third particle test result of the sample to be tested based on at least the third fluorescence signals.

In an embodiment of the disclosure, the optical signal detector 2143 further includes scattered light signal detector (the same scattered light signal detector as the scattered light signal detector described above). The scattered light signal detector is configured to detect scattered light signals from the optical signals, and the processor 2160 is further configured to obtain a third particle test result of the sample to be tested based on the third fluorescence signals and the scattered light signals.

In an embodiment of the disclosure, the two fluorescent dyes include a first fluorescent dye and a second fluorescent dye. A wavelength corresponding to a peak of an emission spectrum of the first fluorescent dye is greater than a wavelength corresponding to a peak of an emission spectrum of the second fluorescent dye; and a difference between a wavelength corresponding to a peak of an emission spectrum of the third fluorescent dye and the wavelength corresponding to the peak of the emission spectrum of the first fluorescent dye is greater than 30 nanometers and less than 80 nanometers, and an overlap between the emission spectra of the third fluorescent dye and the first fluorescent dye is not greater than 50%.

In an embodiment of the disclosure, a wavelength corresponding to a peak of an emission spectrum of the first fluorescent dye is greater than a wavelength corresponding to a peak of an emission spectrum of the second fluorescent dye; a wavelength corresponding to a peak of an emission spectrum of the third fluorescent dye is greater than the wavelength corresponding to the peak of the emission spectrum of the first fluorescent dye or less than the wavelength corresponding to the peak of the emission spectrum of the second fluorescent dye; and the sample analyzer 2100 further includes a second light source (not shown). The second light source is configured to irradiate the particles flowing in the flow cell 2142 by using light with another wavelength such that the particles generate the optical signals including the third fluorescence signals.

In an embodiment of the disclosure, the reagent further includes a hemolytic agent; and the third particle test result comprises a counting result of nucleated red blood cells.

In an embodiment of the disclosure, the processor 2160 is further configured to obtain a proportion of the nucleated red blood cells in all red blood cells in the sample to be tested based on the counting result of the nucleated red blood cells in the sample to be tested.

Based on the above-mentioned description, according to the sample analyzer of the embodiments of the disclosure, a mixed dye including two fluorescent dyes is used for performing particle detection on a sample to be tested. Since a difference between wavelengths corresponding to peaks of emission spectra of the two fluorescent dyes and an overlap between the emission spectra of the two fluorescent dyes are each within a preset range, different cells in the sample to be tested are stained by the different dyes of the mixed dye and then irradiated by a single light source, and different fluorescence signals are then emitted, so that multiple parameters of one sample to be tested can be detected in a single test (in a single reaction channel), thereby improving the detection efficiency. In addition, since multiple parameters of one sample to be tested can be detected in a single reaction channel, the complexity of the liquid path structure of the sample analyzer can be reduced, thereby reducing costs.

Although the exemplary embodiments have been described here with reference to the accompanying drawings, it should be understood that the exemplary embodiments described above are merely exemplary, and are not intended to limit the scope of the disclosure. Those of ordinary skill in the art may make various changes and modifications therein without departing from the scope and spirit of the disclosure. All such changes and modifications are intended to be included in the scope of the disclosure as claimed in the appended claims.

Those of ordinary skill in the art would have appreciated that the units and algorithm steps of the examples described in conjunction with the embodiments disclosed herein may be implemented in electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the disclosure, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this description provided herein. However, it could be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention: namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this description (along with the appended claims, abstract, and drawings) and all the processes or units of any of methods or devices as disclosed. Unless explicitly stated otherwise, each feature disclosed in this description (along with the appended claims, abstract, and drawings) may be replaced by an alternative feature that provides the same, equivalent, or similar objective.

In addition, those skilled in the art should understand that although some of the embodiments described herein include some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules in an article analysis device according to an embodiment of the disclosure. The disclosure may further be implemented as an apparatus program (e.g., a computer program and a computer program product) for executing some or all the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The term "comprising" does not exclude the presence of elements or steps not listed in the claims. The term "a" or "an" preceding an element does not exclude the presence of a plurality of such elements. The disclosure may be implemented by means of hardware including several different elements and by means of an appropriately programmed computer. In unit claims listing several apparatuses, several of these apparatuses may be specifically embodied by one and the same item of hardware. The use of the terms "first", "second", "third", etc. does not indicate any order. These terms may be interpreted as names.

The above descriptions are merely the specific embodiments of the disclosure or the description of the specific embodiments, but the scope of protection of the disclosure is not limited thereto. Any changes or substitutions readily conceivable by those skilled in the art within the technical scope disclosed in the disclosure shall fall within the scope of protection of the disclosure. Therefore, the scope of protection of the disclosure should be subject to the scope of protection of the claims.

What is claimed is:

1. A sample testing method, comprising:
   obtaining a sample to be tested;
   providing a reagent, the reagent comprising a first fluorescent dye and a second fluorescent dye for staining particles in the sample to be tested, wherein an absolute value of a difference between wavelengths corresponding to peaks of emission spectra of the first fluorescent dye and the second fluorescent dye is greater than 30 nanometers and less than 80 nanometers, and an overlap between the emission spectra of the first fluorescent dye and the second fluorescent dye is not greater than 50%;
   mixing the sample to be tested and the reagent for reaction to form a sample solution to be tested;
   flowing the sample solution to be tested flow in a flow cell in a single test, irradiating the particles flowing in the flow cell by using light with a single wavelength such that the particles in the sample to be tested that are stained with the first fluorescent dye and the second fluorescent dye emit first fluorescence signals and second fluorescence signals under the irradiation by the light with the single wavelength, and detecting at least the first fluorescence signals and the second fluorescence signals; and
   obtaining a first particle test result of the sample to be tested based on at least the first fluorescence signals, wherein the first particle test result comprises a classification result and/or a counting result of white blood cells; and
   obtaining a second particle test result of the sample to be tested, based on at least the second fluorescence signals.

2. The method of claim 1, further comprising: detecting scattered light signals, wherein:
   obtaining a first particle test result of the sample to be tested based on at least the first fluorescence signals further comprises: obtaining the first particle test result of the sample to be tested based on the first fluorescence signals and the scattered light signals, and
   obtaining a second particle test result of the sample to be tested based on at least the second fluorescence signal further comprises: obtaining the second particle test result of the sample to be tested based on the second fluorescence signals and the scattered light signals.

3. The method of claim 2, wherein the reagent further comprises a hemolytic agent; and the second particle test result comprises information about reticulocytes.

4. The method of claim 3, wherein the information about the reticulocytes comprises a counting result of reticulocyte fragments.

5. The method of claim 2, wherein the reagent further comprises a diluent; and the first particle test result comprises a classification result and/or a counting result of white blood cells, and the second particle test result comprises a counting result of reticulocytes or comprises a classification result and/or a counting result of red blood cells.

6. The method of claim 1, wherein the absolute value of the difference between the wavelengths corresponding to the peaks of the emission spectra of the first fluorescent dye and the second fluorescent dye is
   greater than 40 nanometers and less than 80 nanometers; or
   greater than 50 nanometers and less than 80 nanometers; or
   greater than 50 nanometers and less than 70 nanometers.

7. The method of claim 1, wherein the overlap between the emission spectra of the first fluorescent dye and the second fluorescent dye is not greater than 35%.

8. The method of claim 7, wherein the overlap between the emission spectra of the first fluorescent dye and the second fluorescent dye is not greater than 15%.

9. The method of claim 1, wherein a difference between wavelengths corresponding to respective peaks of an emission spectrum and an excitation spectrum of at least one of the first fluorescent dye and the second fluorescent dye is
   greater than 30 nanometers; or
   greater than 50 nanometers; or
   greater than 30 nanometers and less than 150 nanometers; or
   greater than 50 nanometers and less than 100 nanometers.

10. A sample analyzer, comprising:
    a sampling portion configured to obtain a sample to be tested and transfer the sample to be tested to a reaction portion;
    a reagent supply portion configured to store a reagent and supply the reagent to the reaction portion as required, wherein the reagent comprises a first fluorescent dye and a second fluorescent dye for staining particles in the sample to be tested, wherein an absolute value of a difference between wavelengths corresponding to peaks of emission spectra of the first fluorescent dye and the second fluorescent dye is greater than 30 nanometers and less than 80 nanometers, and an overlap between the emission spectra of the first fluorescent dye and the second fluorescent dye is not greater than 50%;

the reaction portion comprising a mixing chamber and being configured to mix the sample to be tested and the reagent for reaction to form a sample solution to be tested;

an optical detection system, comprising a first light source, a flow cell, and an optical signal detector, wherein the particles in the sample solution to be tested are capable of flowing in the flow cell in a single test, the first light source is configured to irradiate the particles flowing in the flow cell by using light with a single wavelength such that the particles in the sample to be tested that are stained with the first fluorescent dye and the second fluorescent dye emit first fluorescence signals and second fluorescence signals under the irradiation by the light with the single wavelength, and the optical signal detector comprises a first fluorescence detector and a second fluorescence detector, the first fluorescence detector is configured to detect the first fluorescence signals, and the second fluorescence detector is configured to detect the second fluorescence signals;

a transfer apparatus configured to transfer the sample solution to be tested that has been treated with the reagent in the reaction portion, to the flow cell of the optical detection system; and a processor configured to obtain a first particle test result of the sample to be tested based on at least the first fluorescence signals, wherein the first particle test result comprises a classification result and/or a counting result of white blood cells, and obtain a second particle test result of the sample to be tested based on at least the second fluorescence signals.

11. The sample analyzer of claim 10, wherein the optical signal detector further comprises scattered light signals detector, the scattered light signals detector is configured to detect scattered light signals, and the processor is further configured to obtain the first particle test result of the sample to be tested based on the first fluorescence signal and the scattered light signals, and to obtain the second particle test result of the sample to be tested based on the second fluorescence signal and the scattered light signals.

12. The sample analyzer of claim 11, wherein the reagent further comprises a hemolytic agent; and the second particle test result comprises information about reticulocytes.

13. The sample analyzer of claim 12, wherein the information about the reticulocytes comprises a counting result of reticulocyte fragments.

14. The sample analyzer of claim 11, wherein the reagent further comprises a diluent; and the first particle test result comprises a classification result and/or a counting result of white blood cells, and the second particle test result comprises a counting result of reticulocytes or comprises a classification result and/or a counting result of red blood cells.

15. The sample analyzer of claim 10, wherein the absolute value of the difference between the wavelengths corresponding to the peaks of the emission spectra of the first fluorescent dye and the second fluorescent dye is:

greater than 40 nanometers and less than 80 nanometers; or greater than 50 nanometers and less than 80 nanometers; or greater than 50 nanometers and less than 70 nanometers.

16. The sample analyzer of claim 15, wherein the overlap between the emission spectra of the first fluorescent dye and the second fluorescent dye is not greater than 35%.

17. The sample analyzer of claim 10, wherein a difference between wavelengths corresponding to respective peaks of an emission spectrum and an excitation spectrum of at least one of the first fluorescent dye and the second fluorescent dye is:

greater than 30 nanometers; or greater than 50 nanometers; or greater than 30 nanometers and less than 150 nanometers; or greater than 50 nanometers and less than 100 nanometers.

18. The sample analyzer of claim 10, wherein the reagent further comprises a third fluorescent dye, the optical signal detector further comprises a third fluorescence detector, the third fluorescence detector is configured to detect third fluorescence signals from the optical signals, and the processor is further configured to obtain a third particle test result of the sample to be tested based on at least the third fluorescence signals.

* * * * *